United States Patent [19]
Steinbrink, Jr.

[11] 3,986,834
[45] Oct. 19, 1976

[54] METHOD FOR DETECTING BLOOD UREA NITROGEN

[75] Inventor: Charles F. Steinbrink, Jr., Rockaway, N.J.

[73] Assignee: Becton, Dickinson and Company, East Rutherford, N.J.

[22] Filed: June 4, 1975

[21] Appl. No.: 583,549

[52] U.S. Cl. .......................... 23/230 B; 23/253 R; 23/259; 206/219; 206/223; 252/408
[51] Int. Cl.² ...................................... G01N 33/16
[58] Field of Search .............. 23/253 R, 259, 230 B; 252/408; 206/219, 223

[56] References Cited
UNITED STATES PATENTS

| | | | |
|---|---|---|---|
| 2,709,127 | 5/1955 | Grosskopf | 23/253 R X |
| 3,036,894 | 5/1962 | Forestiere | 23/253 TP X |
| 3,159,586 | 12/1964 | Wildenhayn | 252/408 |
| 3,409,508 | 11/1968 | Hughes | 195/127 |
| 3,446,596 | 5/1969 | Salivar et al. | 23/253 TP |
| 3,475,102 | 10/1969 | Larsen | 23/253 R X |
| 3,511,611 | 5/1970 | Rush | 23/230 B |
| 3,567,374 | 3/1971 | Wybenga | 23/230 B |
| 3,732,077 | 5/1973 | Foster et al. | 23/230 B |
| 3,779,083 | 12/1923 | Ayres et al. | 23/253 R X |
| 3,876,375 | 4/1975 | Maurukas | 252/408 X |

Primary Examiner—Morris O. Wolk
Assistant Examiner—Arnold Turk
Attorney, Agent, or Firm—Kane, Dalsimer, Kane, Sullivan and Kurucz

[57] ABSTRACT

An improved means and method for the determination of blood urea nitrogen in blood serum or plasma. In brief, the means comprises a novel kit, particularly adapted to present a fresh reagent solution of diacetyl, thiosemicarbazide and anhydrous ethylene glycol in individual vessels for analysis and control procedures. The kit is particularly advantageous in that it permits the fresh preparation of reagents in predetermined volumes, for the determination of blood urea nitrogen. The method of the invention comprises employing the kit of the invention for the analysis of unknown specimens of blood serum or plasma.

4 Claims, 5 Drawing Figures

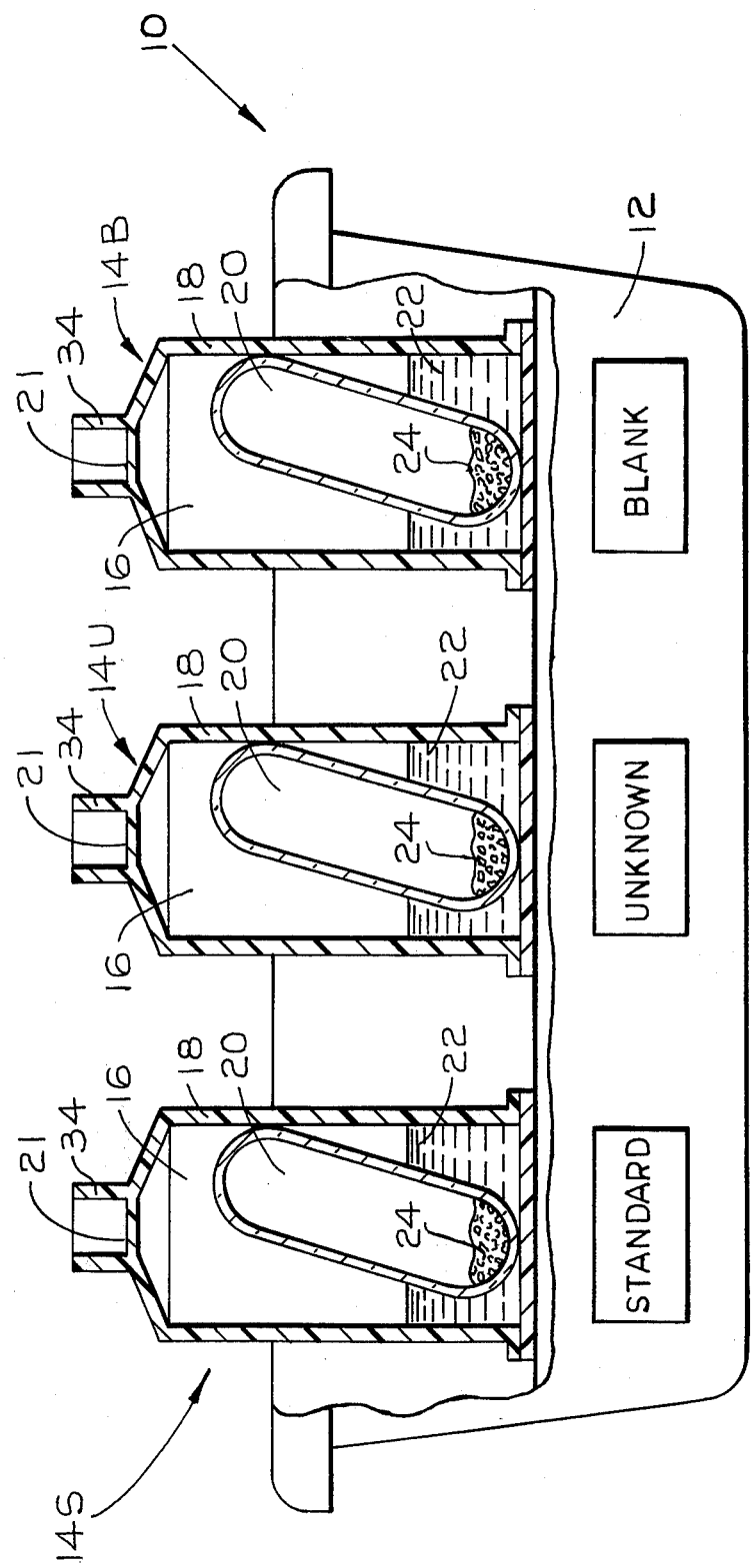

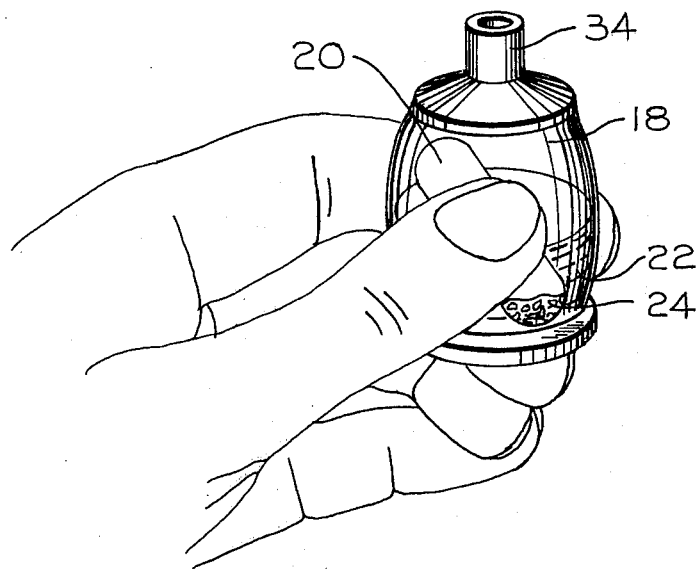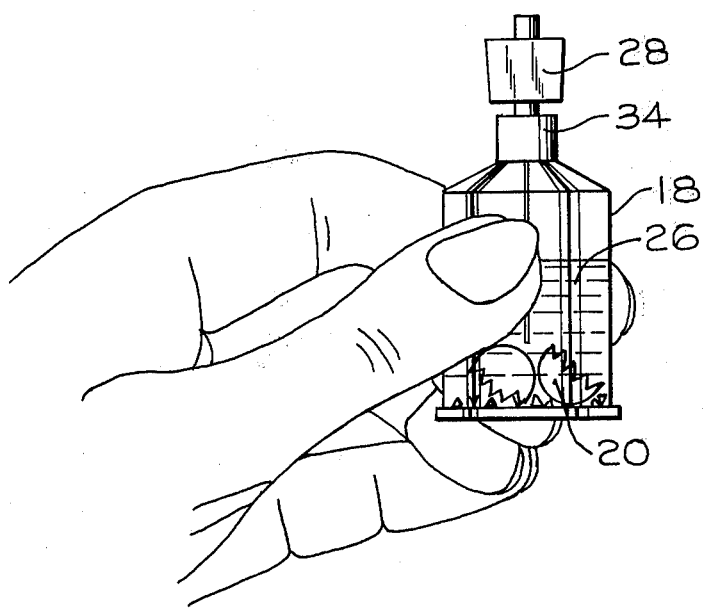

METHOD FOR DETECTING BLOOD UREA NITROGEN

BACKGROUND OF THE INVENTION

1. Field of the Invention

The invention concerns diagnostic procedures performed on biological fluids and more particularly concerns a means and method of determining blood urea nitrogen concentrations in blood serum or plasma.

2. Brief Description of the Prior Art

Colorimetric techniques for the determination of blood urea nitrogen in blood were known prior to this invention; see for example Fearon, Biochem. Journ., 33, pages 902–7 (1939); Coulombe et al., Clinical Chemistry, 9, (1), pages 102–8, (1963); U.S. Pat. Nos. 3,511,611 and 3,732,007. Although the prior art techniques include the use of reagents based on diacetyl, such techniques have required performance by technical personnel having a fairly high degree of technical proficiency. One of the difficulties in blood urea nitrogen determinations employing diacetyl based reagents resides in the fact that diacetyl is relatively unstable. Therefore, the diacetyl based reagent must be freshly prepared immediately before use in carrying out a blood urea nitrogen analysis. Not only is a degree of technical proficiency required for the accurate preparation of a reliable reagent, but such preparation requires additional time and work on the part of the technician prior to his actually carrying out an analysis of an unknown specimen of blood serum or plasma.

The analysis kit of the present invention provides a means whereby a technician is provided with diacetyl reagent precursors in such form that the diacetyl reagent may be immediately prepared with a minimum of effort. The precursor reagents and consequently the kit per se is stable for a period of at least two years when stored out of direct sunlight and at room temperatures. Furthermore, the analysis kit according to the method of this invention provides for the uniform preparation of control reagents. The kit which forms part of this invention also reduces the complexity of the blood urea nitrogen analysis procedure so that it may be carried out by technicians having relatively little experience and training. The result of an analysis carried out employing the kit of the invention are uniform and compare remarkably well with more complex methods of determining blood urea nitrogen.

The method of the invention is particularly advantageous in that it permits for a highly accurate determination of blood urea nitrogen, with the expenditure of a minimum amount of time and effort on the part of technical personnel.

SUMMARY OF THE INVENTION

The invention comprises a kit for use in rapidly determining blood urea nitrogen and which has storage stability over a prolonged period of time, which comprises;

a. three separate reagent reservoirs each of which comprises a flexible walled, closed container having a thin puncturable zone for access to the contents of said reservoirs;

b. an acid catalyst reagent which will promote the conversion of diacetyl monoxime to diacetyl and which will catalyze the reaction of said diacetyl with urea to form a colored complex, disposed in each of said reservoirs;

c. means disposed within each of said reservoirs for enclosing under hermetic conditions a color developing reagent;

d. a color developing reagent consisting essentially of diacetyl monoxime, thiosemicarbazide and an anhydrous, dehydrating diluent having a neutral pH, enclosed by said means;

e. means for bringing said color developing reagent into admixture with said acid catalyst reagent; and f. means for packaging said kit in a unitary package so that all parts will remain conveniently available until needed.

The kit of the invention has a shelf-life stability of at least two years.

The invention also comprises an improved method for the determination of blood urea nitrogen in blood serum or plasma which comprises;

a. providing a kit which comprises,
 1. three separate reagent reservoirs, each containing an acid catalyst reagent which will promote the conversion of diacetyl monoxime to diacetyl and which will catalyze the reaction of said diacetyl with urea to form a colored complex;
 2. means disposed within each of said reservoirs for enclosing under hermetic conditions, a color developing reagent;
 3. a color developing reagent consisting essentially of diacetyl monoxime, thiosemicarbazide and an anhydrous dehydrating diluent having a neutral pH, enclosed by said means;
 4. means for bringing said color developing reagent into admixture with said acid catalyst reagent;

b. activating said means for bringing said color developing reagent into admixture with said acid catalyst reagent in each of the three reservoirs;

c. adding a measured proportion of blood serum or plasma to the mixture of reagents obtained in one of said reservoirs in step (b) above and a measured proportion of urea to the second of said reservoirs;

d. heating the three mixtures contained by said three reservoirs after step (c) above, to a temperature of about 100° C. for a period of from about 10 to about 15 minutes;

e. cooling the heated mixtures of step (d) to a temperature of from about 15° C. to about 20° C. for a period of from about 3 to about 5 minutes;

f. observing the degree of color developed by said color developing reagent in each of said cooled mixtures of step (e), within about 15 minutes of cooling the heated mixture; and g. comparing the degree of color developed in the three mixtures.

BRIEF DESCRIPTION OF THE DRAWINGS

FIG. 1 is a cross-sectional, in part, side elevation of an embodiment kit for the rapid determination of blood urea nitrogen.

FIG. 2 is an isometric view of a vessel component of the embodiment kit shown in FIG. 1, during activation to prepare a fresh reagent for determination of blood urea nitrogen.

FIG. 3 is an isometric view as in FIG. 2 but after introduction of blood serum or plasma to the freshly prepared reagent.

DETAILED DESCRIPTION OF THE INVENTION

Figure 4:
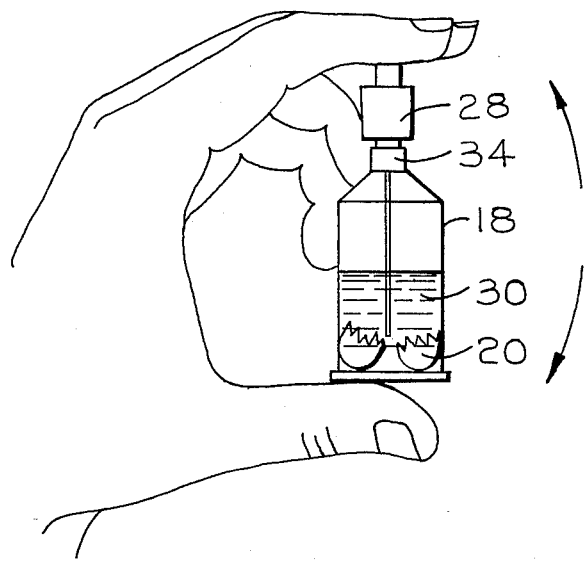
FIG. 4 is an isometric view as seen in FIG. 3, showing mixing of the freshly prepared reagent and a blood serum or plasma specimen.

A complete understanding of the invention may be conveniently had by referring to the accompanying drawings of FIGS. 1-5, inclusive. Referring first to FIG. 1, there is seen a kit 10 which comprises a tray 12 shown cut away, in part, to show in cross-sectional side elevation, three identical vessels 14s, 14u and 14b. Vessel 14s is positioned to correspond to a marker "standard", vessel 14u is positioned in tray 12 to correspond to a marker "unknown" and vessel 14b is positioned adjacent to a marker "blank". Any alternative system of identification may be employed to indicate that one of the three vessels will be employed for the preparation of a standard, one will be employed for the determination of blood urea nitrogen in a specimen of blood serum or plasma and one vessel will be employed as a control blank. For example, the markers may be placed on the appropriate vessels themselves, the vessels may be color coded, or the vessels may be numbered according to an identifiable code. Each vessel 14s, 14u and 14b is a reagent reservoir which comprises a completely enclosed chamber defined by flexible walls, which may be constructed of any flexible polymeric material such as for example, polyethylene, polypropylene and like polymeric materials which are relatively inert chemically and highly flexible. Contained by the flexible walls 18 of each vessel is a frangible capsule 20 and 4.0 milliliters of acid reagent solution 22. Acid reagent solution 22 is prepared by admixture of 1.35 moles of sulfuric acid, 12.3 micromoles of ferric chloride, 9.8 millimoles of phosphoric acid and sufficient distilled water to make one liter of acid reagent solution. Frangible capsule 20 may be a thin walled glass capsule which hermetically seals and encloses 200 microliters of a color developing reagent 24. Color developing reagent 24 is prepared by admixture of 264 micromoles of diacetyl monoxime, 15 micromoles of thiosemicarbazide and sufficient anhydrous, dehydrating diluent such as ethylene glycol (anhydrous) to make up 1 milliliter of solution 24. The ethylene glycol (anhydrous) is a preferred dehydrating diluent which maintains the diacetyl monoxime in stable solution.

Entry into the vessels 14s, 14u and 14b may be obtained by puncturing relatively thin zone 21 in the wall 18 of the vessels. Adjacent to the thin zone 21 is a hub 34 integrally formed with wall 18. Hub 34 is to receive a micropipette as will be discussed hereinafter.

Those skilled in the art will appreciate that the preferred embodiments described above and which comprise a kit 10 within the scope of the invention may be modified in a number of ways without departing from the spirit of the invention. For example, other sizes, shapes and forms of vessels 14s, 14u and 14b may be employed. Similarly, other packaging means such as racks, holders, preformed dishes, and the like may be substituted for tray 12 to provide a unitary package. In addition, additional components may be employed to prepare a kit within the scope of the invention. For example, a puncturing tool may be provided for puncturing thin zone 21 when entry into chamber 16 of any one of the vessels 14s, 14u or 14b is required. A pipette or syringe 28 may also be included in the kit for the transfer of reagent, specimens undergoing analysis and like materials as will be discussed hereinafter. The unitary package provides a convenient means for providing all of the necessary articles for use in carrying out the method of the invention.

To carry out the method of the invention, each of the vessels 14s, 14u and 14b are taken from tray 12, in turn, and the flexible walls 18 squeezed manually as shown in FIG. 2, to break the frangible capsule 20 enclosed in chamber 16. Upon breaking of frangible capsule 20, the color indicating reagent solution 24 is admixed with acid reagent solution 22 to provide a freshly prepared urea-complex forming reagent 26 as shown in FIG. 3. Reagent 26 is diacetyl (I) formed from diacetyl monoxime (II) according to the reaction scheme:

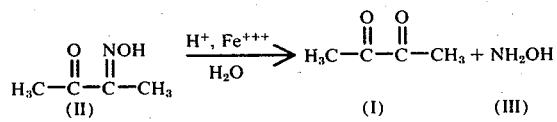

with hydroxylamine (III) by-product.

Reagent 26 is useful for the detection of urea since the diacetyl (I) forms a red colored complex (IV) upon condensation with urea (V) according to the scheme:

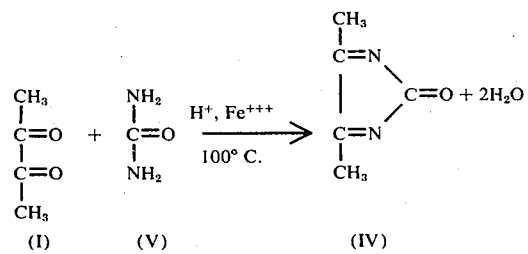

The complex (IV) formed is red in color and the thiosemicarbazide presence intensifies development of that color.

Within 36 hours following the fresh preparation of reagent 26 by admixture of reagents 22 and 24 a puncture is made in thin zone 21 of each of the vessels 14s, 14u and 14b. Through the puncture in vessel 14s, 13 microliters of a urea nitrogen standard is introduced. The urea nitrogen standard is prepared by dissolving a known proportion of urea in distilled water so that the concentration of urea in the standard solution is known. Into the chamber 16 of vessel 14u there is introduced through the puncture therein, 13 microliters of blood serum or blood plasma to be tested for its blood urea nitrogen content. The vessel 14b is a control vessel and does not receive any foreign matter for admixture with the reagent 26 found therein. A convenient means of introducing the serum, plasma or standard solution into the vessels 14s and 14u is with a measuring micropipette 28 adapted to mate with and be received by hub 34 as shown in FIG. 3. After the urea standard solution or unknown blood serum or plasma is introduced into the appropriate vessel 14s and 14u, the vessels are shaken to assure a complete mixture of urea complex forming reagent 26 with the added unknown and standard solutions. As shown in FIG. 4, a convenient method of carrying out the admixture is by shaking each vessel 14s and 14u manually with micropipette 28 in place, whereupon there is obtained reaction mixture 30. The micropipette 28 is retained in place as a convenience to close the puncture made in each vessel 14s and 14u.

Figure 5:
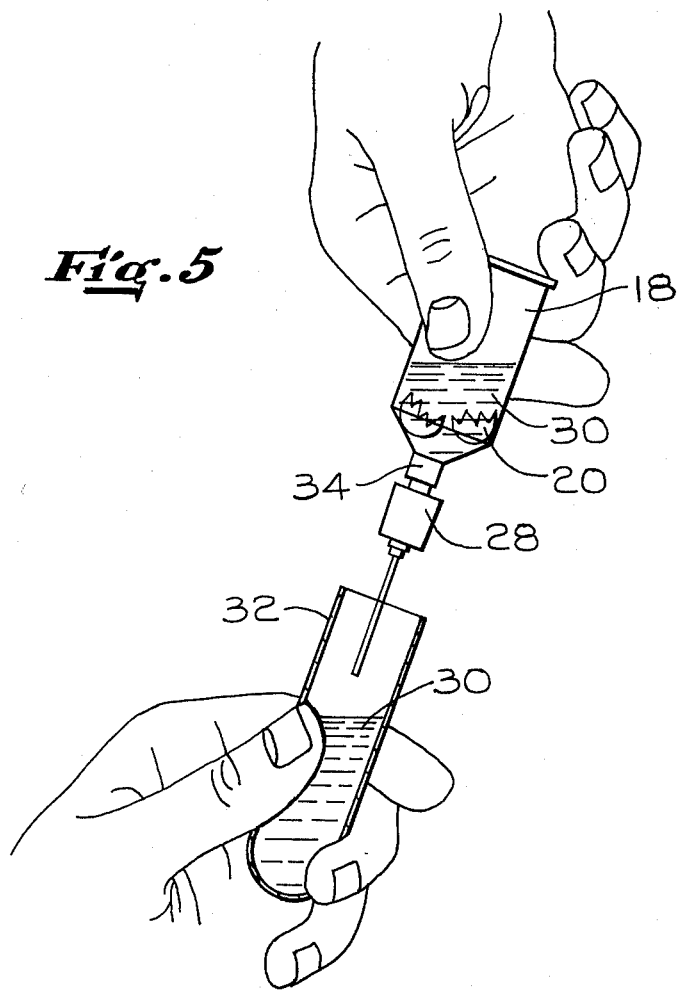
FIG. 5 shows transfer of the mixed blood serum or plasma with reagent, to a test tube for further processing according to the method of the invention.

Following the preparation of reaction mixture 30 [which consists of urea complex forming reagent 26 with either the unknown blood serum or blood plasma (in vessel 14u) or a nitrogen urea standard (in vessel 14s)] reaction mixture 30 is transferred from each of vessels 14s, 14u and reagent 26 is transferred from vessel 14b, to a correspondingly identified or labeled test tube 32. As shown in FIG. 5, transfer may be conveniently carried out by reversing micropipette 28 in hub 34 and squeezing walls 18 to force the transfer. Each of the mixtures 30 from vessels 14s and 14u and reagent 26 from vessel 14b are then heated in separate test tubes 32 with an appropriate heating device, such as a boiling water bath, to a temperature of about 100° C. for a period of from about 10 to about 15 minutes. At the end of this period of time, the reaction mixtures 30 and reagent mixture 26 are cooled to a temperature of from about 15° to about 20° C. The three separate mixtures are then allowed to stand at this lower temperature for a period of from about 3 to about 5 minutes. Immediately upon expiration of this period of time, the three cooled solutions are transferred to separate cuvettes labeled according to the corresponding vessels 14s, 14u and 14b from which they originated. The cuvettes are inserted in the reading station of a spectrophotometer for the measurement of the light absorbance of the contained mixtures. Setting the wavelength on the spectrophotometer at 520 nm, maximum optical density measurements on each of the three mixtures are obtained. The measurement should be taken within at least 15 minutes after the solutions have been cooled to 15° – 20° C.

After determining the maximum optical density of the unknown reaction mixture 30 (from vessel 14u) and the urea standard reaction mixture 30 from 14s vessel, the concentration of urea nitrogen in the unknown may be calculated according to the formula:

$$\begin{bmatrix}\text{urea nitrogen, mg/dl}\\ \text{of unknown}\end{bmatrix} = \frac{\text{absorbance of unknown}}{\text{absorbance of standard}} \times \begin{bmatrix}\text{urea}\\ \text{concentration}\\ \text{of standard,}\\ \text{mg/dl}\end{bmatrix}$$

The mixture carried through the above procedure from reservoir vessel 14b is the control blank and should present a clear to pale amber color. If there is a notable discoloration, there is an indication that the analysis procedure was contaminated, and a re-analysis is warranted.

What is claimed is:

1. An improved method for the determination of blood urea nitrogen in blood serum or plasma, which comprises;

a. providing three separate reagent reservoirs, each containing
        (i) an acid catalyst reagent which will promote the conversion of diacetyl monoxime to diacetyl and which will catalyze the reaction of said diacetyl with urea to form a colored complex; and each containing
        (ii) a frangible capsule disposed within each of said reservoirs for enclosing under hermetic conditions
        (iii) a color developing reagent;
    such color developing reagent consisting essentially of diacetyl monoxime, thiosemicarbazide and anhydrous ethylene glycol being so enclosed by said frangible capsule;
    b. breaking said capsule within each of said reservoirs thereby bringing said color developing reagent into admixture with said acid catalyst reagent in each of the three reservoirs;
    c. adding a measured proportion of blood serum or plasma to the mixture of reagents obtained in one of said reservoirs in step (b) above and a measured proportion of urea to a second of said reservoirs;
    d. heating the three mixtures contained by said three reservoirs after step (c) above, to a temperature of about 100° C. for a period of from about 10 to about 15 minutes;
    e. cooling the heated mixtures of step (d) to a temperature of from about 15° C. to about 20° C. and allowing the cooled mixtures to stand for a period of from about 3 to about 5 minutes;
    f. observing the degree of color developed by said color developing reagent in each of said cooled mixtures of step (e), within about 15 minutes of cooling the heated mixture; and
    g. comparing the degree of color developed in the three mixtures.

2. A method according to claim 1 wherein said acid catalyst reagent consists essentially of sulfuric acid, phosphoric acid and ferric chloride in an aqueous mixture.

3. A method according to claim 1 wherein said observing is with the aid of a spectrophotometer.

4. A storage stable diacetyl monoxime liquid composition which comprises in admixture diacetyl monoxime, thiosemicarbazide and anhydrous ethylene glycol stored under hermetic conditions.

* * * * *